US012728134B2

(12) United States Patent
Wagner et al.

(10) Patent No.: US 12,728,134 B2
(45) Date of Patent: Sep. 8, 2026

(54) LIQUISOLID PHARMACEUTICAL FORMULATION AND PROCESS FOR MANUFACTURING

(71) Applicant: RHEINISCHE FRIEDRICH-WILHELMS-UNIVERSITÄT BONN, Bonn (DE)

(72) Inventors: Karl G. Wagner, Bonn (DE); Alf Lamprecht, Wesseling (DE); Anna Katharina Krome, Bonn (DE); Daris Grisic, Düsseldorf (DE); Alexander Denninger, Unterensingen (DE); Tim Becker, Bonn (DE)

(73) Assignee: RHEINISCHE FRIEDRICH-WILHELMS-UNIVERSITÄT BONN (DE)

( * ) Notice: Subject to any disclaimer, the term of this patent is extended or adjusted under 35 U.S.C. 154(b) by 792 days.

(21) Appl. No.: 17/922,053

(22) PCT Filed: Apr. 29, 2021

(86) PCT No.: PCT/EP2021/061328
§ 371 (c)(1),
(2) Date: Oct. 28, 2022

(87) PCT Pub. No.: WO2021/219817
PCT Pub. Date: Nov. 4, 2021

(65) Prior Publication Data

US 2023/0165879 A1 Jun. 1, 2023

(30) Foreign Application Priority Data

Apr. 30, 2020 (EP) .................................... 20172440

(51) Int. Cl.

| | |
|---|---|
| ***A61K 31/635*** | (2006.01) |
| ***A61K 9/16*** | (2006.01) |
| ***A61K 31/192*** | (2006.01) |
| ***A61K 31/216*** | (2006.01) |
| ***A61K 31/4422*** | (2006.01) |
| ***A61K 31/4545*** | (2006.01) |
| ***A61K 47/10*** | (2017.01) |

(52) U.S. Cl.
CPC .......... *A61K 31/635* (2013.01); *A61K 9/1611* (2013.01); *A61K 9/1617* (2013.01); *A61K 9/1676* (2013.01); *A61K 31/192* (2013.01); *A61K 31/216* (2013.01); *A61K 31/4422* (2013.01); *A61K 31/4545* (2013.01); *A61K 47/10* (2013.01)

(58) Field of Classification Search
None
See application file for complete search history.

(56) References Cited

FOREIGN PATENT DOCUMENTS

| | | | |
|---|---|---|---|
| CN | 102083467 | * | 6/2011 |
| DE | 10 2015 008 534 A1 | | 5/2017 |

OTHER PUBLICATIONS

Patra et al. "An Overview of liquisolid technology".*
Grizic et al. "Propylene carbonate quantification by its derivative 3,5-diacetyl-1,4-dihydro-2,6 lutidine".*
Patra et al. "An Overview of liquisolid technology" 2015.*
Grizic et al. "Porous Carriers for Controlled/Modulated Drug Delivery". 2016.*
Tiong et al. "Effects of liquisolid formulations on dissolution of naproxen" 2009.*
Porous Carriers for Controlled/Modulated Drug Delivery 2009.*
International Search Report mailed Jul. 9, 2021 from corresponding International Application No. PCT/EP2021/061328.
Extended European Search Report mailed on Oct. 16, 2020 from corresponding European Application No. 20172440.8.
Chinam Niranjan Patra, et al., "An overview of liquisolid technology", Pharmaceutical drug delivery systems and vehicles, Woodhead Publishing India PVT. Ltd, India, pp. 146-160, Nov. 16, 2015.
Raymond C Rowe, et al., "Propylene Carbonate", Handbook of Pharmaceutical Excipients—5$^{th}$ edition, pp. 622-623, 2006.
Bao Chen, et al., "In vitro and in vivo evaluation of ordered mesoporous silica as a novel adsorbent in liquisolid formulation", International Journal of Nanomedicine, p. 199, 2012.
Mei Lu, et al., "Liquisolid technique and its applications in pharmaceutics", Asian Journal of Pharmaceutical Sciences, vol. 12, No. 2, pp. 115-123, Nov. 4, 2016.
Barbora Vranikova, et al., "Mechanistic aspects of drug loading in liquisolid systems with hydrophilic lipid-based mixtures", International Journal of Pharmaceutics, Elsevier, NL, vol. 578, Jan. 30, 2020.
Alexander Denninger, et al., "A Rational Design of a Biphasic Dissolution Setup—Modelling of Biorelevant Kinetics for a Ritonavir Hot-Melt Extruded Amorphous Solid Dispersion", Pharmaceutics, 12, 237, 2020.
Bukara K et al., "*Order Mesoporous Silica To Enhance The Bioavailability Of Poorly Water Soluble Drugs: Proof Of Concept In Man*", European Journal of Pharmaceutics and Biopharmaceutics, vol. 108, pp. 220-225, (2016).
McCarthy, Carol A et al., "*In Vitro Dissolution Models For The Prediction Of In Vivo Performance Of An Oral Mesoporous Silica Formulation*", Journal of Controlled Release, vol. 250, pp. 86-95, (2017).

(Continued)

*Primary Examiner* — Danah Al-Awadi
(74) *Attorney, Agent, or Firm* — Davidson Kappel LLC

(57) ABSTRACT

The present invention relates to a liquisolid pharmaceutical formulation comprising a porous carrier and an active pharmaceutical ingredient loaded onto a surface of the porous carrier, wherein the active pharmaceutical ingredient is dispersed in propylene carbonate or a mixture of propylene carbonate and a further solvent and the dispersion of the active pharmaceutical ingredient and propylene carbonate or a mixture of propylene carbonate and a further solvent is loaded onto the external surface and the internal surface located inside the pores of the porous carrier thereby forming a liquisolid system, and to a process for manufacturing such a liquisolid pharmaceutical formulation.

20 Claims, 3 Drawing Sheets

(56) References Cited

OTHER PUBLICATIONS

Figure 1:
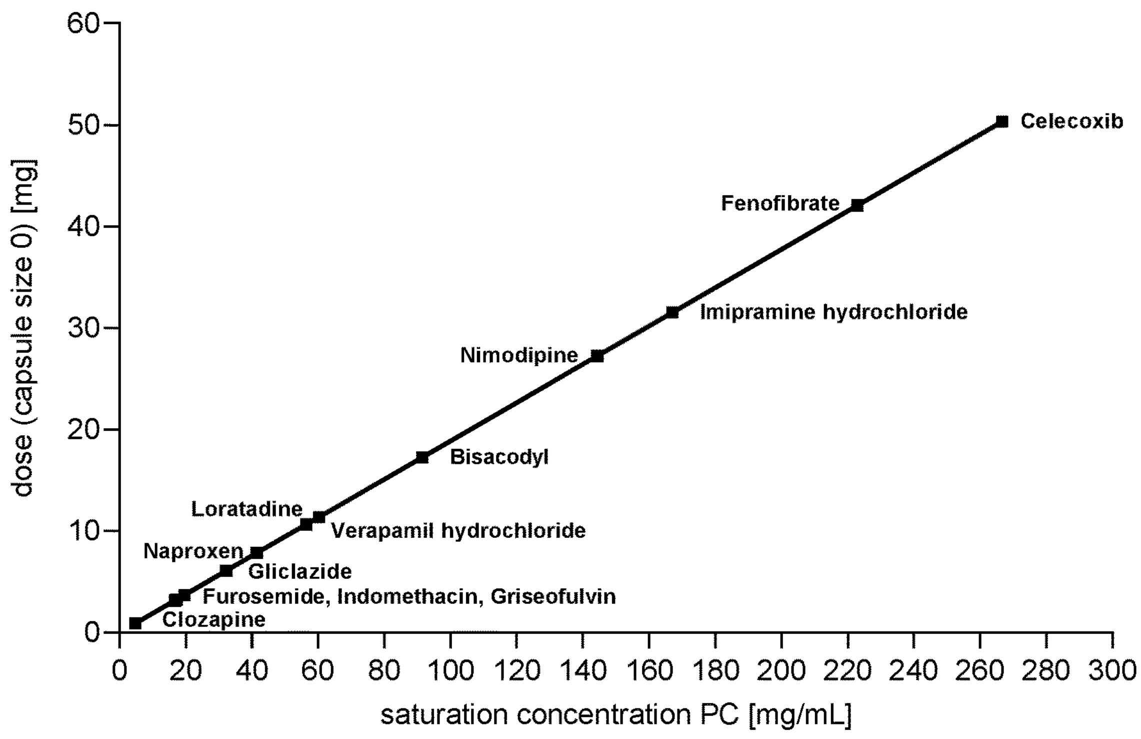

Extended European Search Report mailed on Oct. 15, 2020 from corresponding European Application No. 20172440.8.
International Written Opinion mailed Jul. 9, 2021 from corresponding International Application No. PCT/EP2021/061328.
International Preliminary Report on Patentability issued on Oct. 27, 2022 from corresponding International Application No. PCT/EP2021/061328.

* cited by examiner

LIQUISOLID PHARMACEUTICAL FORMULATION AND PROCESS FOR MANUFACTURING

This application is a U.S. national phase application under 35 U.S.C. of § 371 of International Application No. PCT/EP2021/061328, filed Apr. 29, 2021, which claims priority of European Patent Application No. EP 20172440.8, filed Apr. 30, 2020, the disclosures of which are hereby incorporated by reference herein.

The present invention relates to a liquisolid pharmaceutical formulation.

Solubility is one of the important parameters for the oral bioavailability of pharmaceutical ingredients. The oral route is preferred for administration because of patient compliance, convenience, and low cost factor. When administered via the oral route, the active pharmaceutical ingredient (API) should be sufficiently dissolved in gastric fluids for its proper absorption. Since only dissolved substances are diffused or transported into the blood via the gastrointestinal tract, an improvement in oral bioavailability can be achieved by improving the solubility of poorly water-soluble active ingredients. Thus, one of the challenges is producing formulations with adequate oral bioavailability and therapeutic effectiveness, particularly for active pharmaceutical ingredients that exhibit low aqueous solubility.

Bukara K et al. describe in the European Journal of Pharmaceutics and Biopharmaceutics, 2016; 108, 220-225 an improvement in the bioavailability of the active ingredient fenofibrate by adsorption on an inorganic carrier material in the form of mesoporous silicate in humans. Also, Carol A. McCarthy et al. describe in J Control Release, 2017, 250, 86-95 an oral mesoporous silica formulation of fenofibrate. Supported by a solvent, the active ingredient can penetrate into the pores of the mesoporous silicate, creating a liquid-solid system (liquisolid). The non-volatile solvents such as polyethylene glycol, polysorbate, propylene glycol or glycerine used in the liquisolid system mainly act as a binding agent. However, the choice of solvent for the production of the liquid-solid system is limited, since the solvent needs to provide low toxicity, low viscosity and a sufficient solubility.

DE 10 2015 008 534 A1 describes pharmaceutical formulations using propylene carbonate together with polyesters for micro-particle formulations. However, the polyester is solved in the propylene carbonate, which in part reacts to propylene glycol.

Therefore, the objective underlying the present invention was to provide a formulation with improved solubility for poorly soluble active ingredients.

The problem is solved by a liquisolid pharmaceutical formulation comprising a porous carrier and an active pharmaceutical ingredient loaded onto a surface of the porous carrier, wherein the active pharmaceutical ingredient is dispersed in propylene carbonate or a mixture of propylene carbonate and a further solvent and the dispersion of the active pharmaceutical ingredient and propylene carbonate or a mixture of propylene carbonate and a further solvent is loaded onto the external surface and the internal surface located inside the pores of the porous carrier thereby forming a liquisolid system.

The liquisolid pharmaceutical formulation based on propylene carbonate and a porous carrier such as mesoporous silica provides a fast availability of the active pharmaceutical ingredient from the formulation. This provides a faster pharmaceutical effect of the ingredient and further can provide for better bioavailability. Better bioavailability reduces the amount of the ingredient needed to achieve the pharmaceutical effect, which results in lesser local side effects in the gastrointestinal tract, a better safety due to lesser individual variations of efficacy, and a cost-effective manufacture due to fewer amounts of the ingredient.

The term "liquisolid system" refers to formulations formed by conversion of liquid drugs, drug suspensions or drug solutions in non-volatile solvents, into dry, non-adherent, free flowing or particulate and compressible powder mixtures by blending the suspension or solution with selected carriers. The concept of liquisolid technique relies on that when a drug dissolved in the liquid vehicle is incorporated into a carrier material which has a porous surface, loading such as adsorption of the liquid onto the internal and external surfaces of the porous carrier particles occur. The carrier material having high adsorptive properties and large specific surface area gives the liquisolid system the desirable flow characteristics.

In embodiments, the porous carrier is selected from porous silica, polyorganosiloxanes, pharmaceutical clays, silicon dioxide nanotubes, silica gel, magnesium aluminosilicate, anhydrous calcium phosphate, and calcium carbonate. These carriers provide for adsorptive properties and large specific surface area useful for the manufacture of a liquisolid system. The active pharmaceutical ingredient needs to be loaded onto a surface of the porous carrier, and preferably, is adsorbed onto the surface of the porous carrier. Particularly porous silica allows for good adsorptive properties. Preferably, the porous carrier is selected from mesoporous, microporous silica and macroporous silica. In preferred embodiments, the porous carrier is mesoporous silica. Mesoporous silica advantageously allows for the active pharmaceutical ingredient to be adsorbed onto the silica surface.

Propylene carbonate provides low toxicity and low viscosity, which features allow for a use in the manufacture of the liquisolid pharmaceutical formulation. Propylene carbonate may be used as the only matrix for the ingredient or may be used in the form of a mixture together with a further solvent. In embodiments, the further solvent is selected from dimethyl sulfoxide (DMSO), ethanol, methanol, isopropanol, dichloromethane, acetone, tert-butanol, or a polymer which is liquid at ambient temperature (20±2° C.) such as a polyethylene glycol (PEG) preferably selected from PEG 400, PEG 300 and PEG 200. These solvents are usable for a multitude of active pharmacological ingredients, particularly for poorly water-soluble or water-insoluble compounds. Preferred further solvents are selected from dimethyl sulfoxide (DMSO) and ethanol. In other embodiments, the further solvent is tetraethylene glycol (tetraglycol).

In embodiments, the active pharmaceutical ingredient is a poorly water-soluble or water-insoluble compound, preferably selected from the group comprising nimodipine, celecoxib, fenofibrate, naproxen, loratadine, imipramine, bisacodyl, gliclazide, furosemide, clozapine, and mixtures thereof. In a pharmaceutical context the term "poor water-solubility" is understood as meaning that the highest dose strength of a compound cannot be dissolved in 250 mL water in the pH range between 1 and 6.8 at 37±1° C. according to the Biopharmaceutics Classification System (BCS). Poorly water-soluble or water-insoluble active pharmaceutical ingredients, however, may be dispersed and advantageously dissolved in propylene carbonate and further solvents, particularly such as dimethyl sulfoxide (DMSO) and ethanol. Preferably, the active pharmaceutical ingredient is dissolvable or is dissolved in propylene carbonate.

In embodiments, the active pharmaceutical ingredient is loaded to the porous carrier in an amount in a range of ≥5 weight % to ≤70 weight %, preferably in an amount in a range of ≥20 weight % to ≤50 weight %, based on a weight of 100 weight % of the liquisolid pharmaceutical formulation comprising the porous carrier, the active pharmaceutical ingredient and propylene carbonate. These high amounts of the active ingredient in the formulation provide a considerable advantage of the liquisolid pharmaceutical formulation.

In embodiments, propylene carbonate is comprised in an amount in a range of ≥10 weight % to ≤60 weight %, preferably in an amount in a range of ≥30 weight % to ≤50 weight %, based on a weight of 100 weight % of the porous carrier and propylene carbonate. In these ranges, stable semisolid systems can be provided, which show good flow properties. In preferred embodiments, propylene carbonate may be comprised in an amount of 45 weight % to 50 weight %, based on a weight of 100 weight % of mesoporous silica and propylene carbonate.

A further aspect of the present invention relates to a pharmaceutical solid dosage form, comprising the liquisolid pharmaceutical formulation according to the invention. In embodiments, the solid dosage form is selected from a capsule, a tablet, granules, pills, pellets or micro-tablets.

A further aspect of the present invention relates to a process for manufacturing a liquisolid pharmaceutical formulation, the process comprising the steps of:

a) dispersing, dissolving or otherwise introducing an active pharmaceutical ingredient into propylene carbonate or a mixture of propylene carbonate and a further solvent to form a liquid mixture,
b) selecting a porous carrier, and
c) admixing the liquid mixture of step a) and the porous carrier of step b) to form a liquisolid formulation The formulation can be manufactured with little effort and standard equipment and thus is useful for preclinical and clinical development of pharmaceutical ingredients. Also, industrial processing is possible in energy and cost-effective, particularly compared to the manufacture of amorphous solid dispersions.

Optionally, excess propylene carbonate or a mixture of propylene carbonate and a further solvent from the mixture obtained in step c) may be removed. It is however, preferred to add only as much liquid mixture to the porous carrier, which can be adsorbed. Excess propylene carbonate or solvent mixture may, for example, be removed by evaporating, such as by using vacuum drying, at e.g. elevated temperatures.

The liquisolid pharmaceutical formulation may be orally administered. It is however, preferred to further formulate the liquisolid pharmaceutical formulation into a usual pharmaceutical solid dosage form, such as a capsule, granules, or a tablet. In embodiments of the process, in a further step d) the liquisolid formulation is formed into capsules, tablets, granules, pills, pellets, or micro-tablets, preferably into capsules, granules or tablets. In embodiments, the process thus is a process for manufacturing capsules, tablets, granules, pills, pellets, or micro-tablets, preferably capsules, granules, or tablets comprising the liquisolid pharmaceutical formulation.

For manufacturing capsules, tablets or granules, the liquisolid formulation can be filled into capsules; mixed with tableting additives and compressed to tablets; or granules can be formed by wet or dry granulation, respectively. These methods are standard procedures known to a person skilled in the art and, for example, may be performed using standard equipment such as usual tableting machines.

In embodiments, the admixing in step c) is performed at a temperature in a range from ≥10° C. to ≤50° C., preferably in a range from ≥15° C. to ≤30° C. In these temperature ranges, good results were achieved.

In embodiments of the process, in step a) the dispersing, dissolving or otherwise introducing an active pharmaceutical ingredient into propylene carbonate or a mixture of propylene carbonate and a further solvent is performed by ultrasonic dissolving, vortexing, or mixing using magnetic mixers or blade agitators.

The porous carrier may be selected from mesoporous, microporous silica, macroporous silica, polyorganosiloxanes, pharmaceutical clays, silicon dioxide nanotubes, silica gel, magnesium aluminosilicate, anhydrous calcium phosphate, and calcium carbonate. Preferably, the porous carrier is selected from mesoporous, microporous silica, and macroporous silica. In preferred embodiments, the porous carrier is mesoporous silica. The further solvent may be selected from dimethyl sulfoxide (DMSO), ethanol, methanol, isopropanol, dichloromethane, acetone, tert-butanol, or a polymer which is liquid at ambient temperature (20±2° C.) such as a polyethylene glycol (PEG) preferably selected from PEG 400, PEG 300 and PEG 200. In other embodiments, the further solvent is tetraethylene glycol (tetraglycol).

Preferred further solvents are dimethyl sulfoxide (DMSO) and ethanol. The active pharmaceutical ingredient may be a poorly water-soluble or water-insoluble compound, such as an active pharmaceutical ingredient having a log P value of from 2 to 6, preferably selected from the group comprising nimodipine, celecoxib, fenofibrate, naproxen, loratadine, imipramine, bisacodyl, gliclazide, furosemide, clozapine and mixtures thereof. For the further description of the liquisolid pharmaceutical formulation, the active pharmaceutical ingredients, further solvents and porous carrier, used in the method, reference is made to the description above.

A further aspect of the present invention relates to a liquisolid pharmaceutical formulation or a pharmaceutical solid dosage form obtained by the process according to the invention. For the description of the liquisolid pharmaceutical formulation and the pharmaceutical solid dosage forms, reference is made to the description above. Preferred pharmaceutical solid dosage forms are selected from a capsule, a tablet, granules, pills, pellets, or micro-tablets.

Unless otherwise defined, the technical and scientific terms used herein have the same meaning as commonly understood by one of ordinary skill in the art to which this invention belongs.

The Examples, which follow serve to illustrate the invention in more detail but do not constitute a limitation thereof.

The figures show:

FIG. 1 The maximum deliverable dose of various poorly water-soluble active pharmaceutical ingredients in propylene carbonate (PC).

Figure 2:
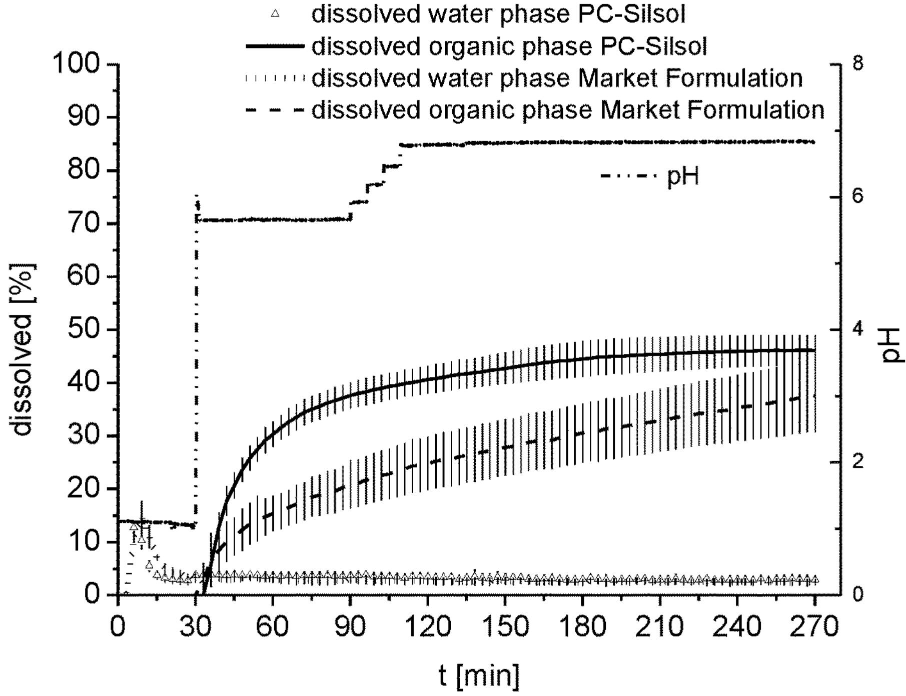

FIG. 2 The biphasic dissolution profiles of a liquisolid pharmaceutical formulation of Nimodipine compared to a Nimodipine market formulation.

Figure 3:
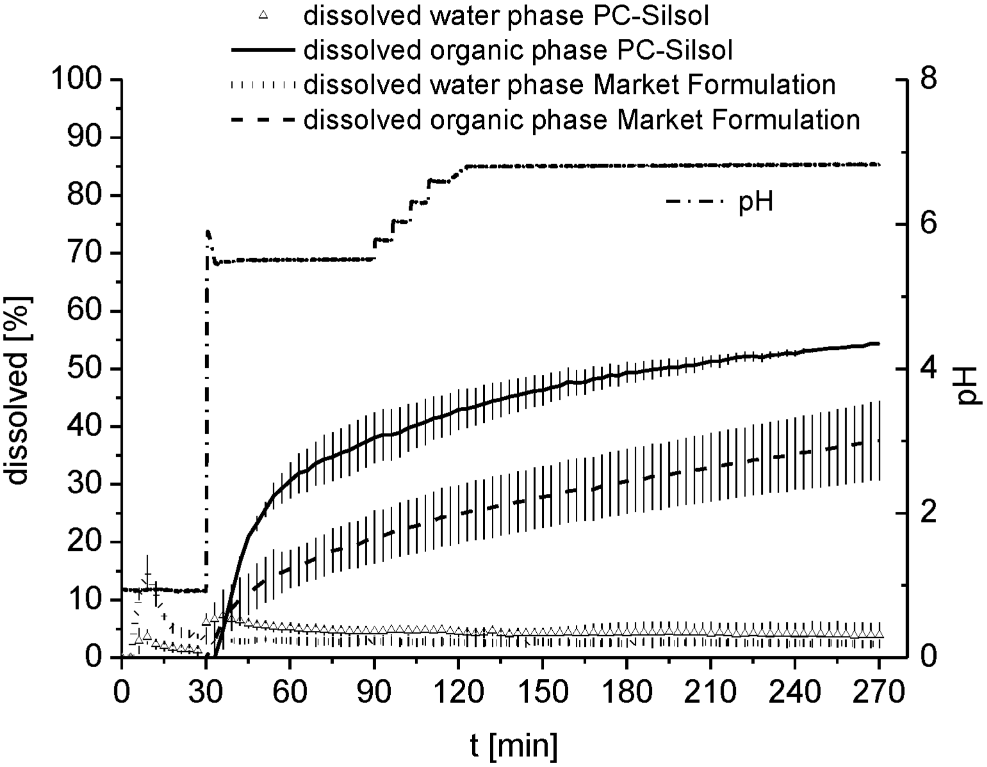

FIG. 3 The biphasic dissolution profiles of a liquisolid pharmaceutical formulation of Celecoxib compared to a Celecoxib market formulation.

Figure 4:
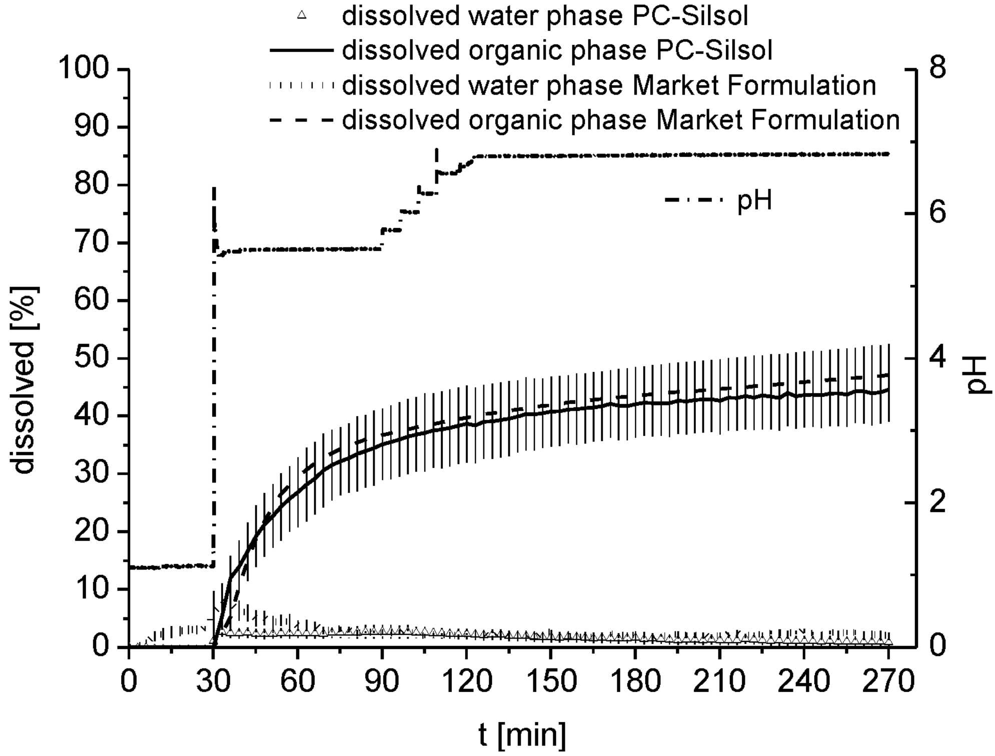

FIG. 4 The biphasic dissolution profiles of a liquisolid pharmaceutical formulation of Fenofibrate compared to a Fenofibrate market formulation.

Figure 5:
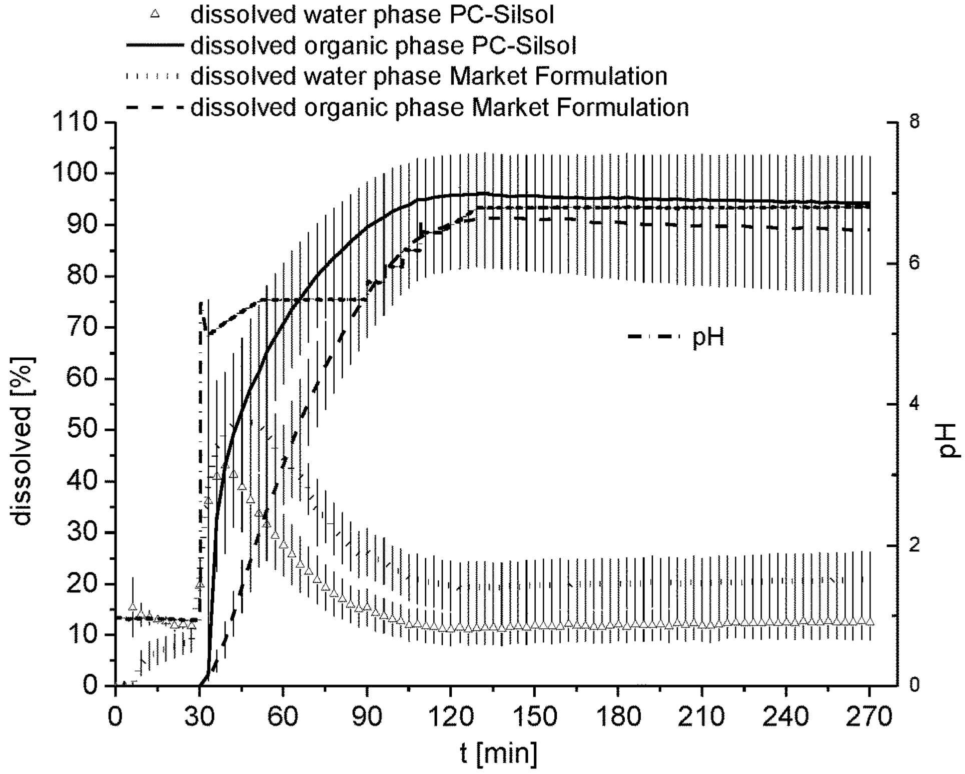

FIG. 5 The biphasic dissolution profiles of a liquisolid pharmaceutical formulation of Naproxen compared to a Naproxen market formulation.

Figure 6:
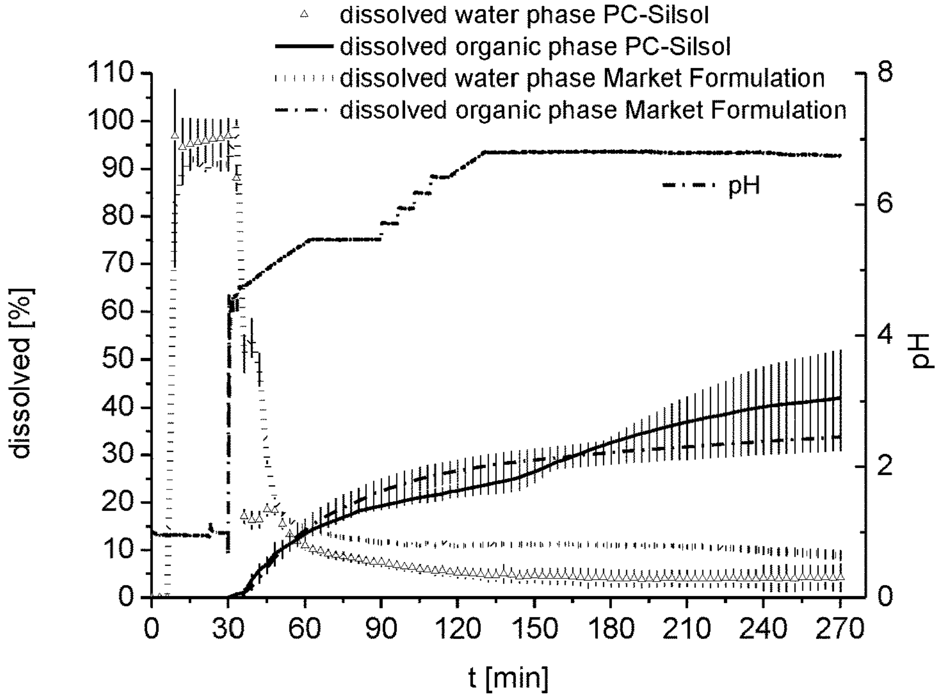

FIG. 6 The biphasic dissolution profiles of a liquisolid pharmaceutical formulation of Loratadine compared to a Loratadine market formulation.

EXAMPLE 1: SOLUBILITY ANALYSIS OF POORLY WATER-SOLUBLE DRUGS IN PROPYLENE CARBONATE

To determine suitable drug candidates, the solubility of various poorly water-soluble active pharmaceutical ingredients (API) in propylene carbonate was tested. For a preliminary analysis, 1-2 mg of each compound was weighted in an Eppendorf tube and 1 ml propylene carbonate was added. The mixture was mixed with a metal spatula for 10 min each. The solubility of compounds, which were fully dissolved in the preliminary tests where than further analyzed. About 20 mg of each compound were used and under stirring with a metal spatula propylene carbonate was added in 10 μl steps. The following table 1 shows the results of the solubility tests.

TABLE 1

Solubility of poorly water-soluble active pharmaceutical ingredients (API) in propylene carbonate

| Active Pharmaceutical Ingredient | Sample [mg] | Solvent [mL] | Mean Solubility [mg/mL] |
|---|---|---|---|
| Bisacodyl (Sigma-Aldrich Chemie GmbH, Steinheim, Germany) | 22.40<br>22.30<br>20.30 | 0.25<br>0.24<br>0.22 | 91.55 |
| Celecoxib (Kekule Pharma Limited, Hyderabad, India) | 21.90<br>21.20<br>20.90 | 0.10<br>0.07<br>0.07 | 266.67 |
| Clozapine (Swapnroop Drugs and Pharmaceuticals, Aurangabad, India) | 20.60<br>20.50<br>21.20 | 4.30<br>4.30<br>4.40 | 4.79 |
| Fenofibrate (≥99%, Sigma-Aldrich Chemie GmbH, Steinheim, Germany) | 21.20<br>20.30<br>20.90 | 0.12<br>0.08<br>0.08 | 222.86 |
| Furosemide (Sigma-Aldrich Chemie GmbH, Traufstein, Germany) | 20.30<br>20.00<br>20.50 | 1.04<br>1.07<br>1.00 | 19.55 |
| Gliclazide (≥98%, Sigma-Aldrich Chemie GmbH, Steinheim, Germany) | 23.60<br>24.30<br>23.10 | 0.74<br>0.76<br>0.70 | 32.27 |
| Griseofulvin (97%, Alfa Aesar GmbH & Co KG, Karlsruhe, Germany) | 20.10<br>22.40<br>20.70 | 1.20<br>1.32<br>1.24 | 16.81 |
| Imipramine hydrochloride (≥99%, Sigma-Aldrich Chemie GmbH, Steinheim, Germany) | 9.70<br>19.90<br>20.50 | 0.06<br>0.11<br>0.13 | 167.00 |
| Indomethacin (98%, Alfa Aesar GmbH & Co KG, Karlsruhe, Germany) | 11.40<br>10.50<br>10.30 | 0.70<br>0.60<br>0.57 | 17.22 |
| Loratadine (Sris Pharmaceuticals, Hyderabad, India) | 20.20<br>21.80<br>20.60 | 0.35<br>0.35<br>0.35 | 60.19 |
| Naproxen (Sigma-Aldrich Chemie GmbH, Steinheim, Germany) | 19.80<br>23.50<br>22.30 | 0.46<br>0.58<br>0.54 | 41.52 |
| Nimodipine (≥98%, Tokyo Chemical Industrie, Zwijndrecht, Belgium) | 23.10<br>25.70<br>23.40 | 0.16<br>0.18<br>0.16 | 144.40 |
| (+)- Verapamil hydrochloride (≥99%, Sigma-Aldrich Chemie GmbH, Steinheim, Germany) | 19.40<br>22.30<br>21.40 | 0.34<br>0.40<br>0.38 | 56.34 |

FIG. 1 shows the maximum deliverable dose of the active pharmaceutical ingredients (table 1) in propylene carbonate (PC) which can be administered in a single capsule (Size 0). Nimodipine, celecoxib, fenofibrate, naproxen and loratadine were elected for the manufacture of liquisolid pharmaceutical formulations and further testing.

EXAMPLE 2: MANUFACTURE OF LIQUISOLID PHARMACEUTICAL FORMULATIONS BY ADSORPTION TO MESOPOROUS SILICA

The respective active pharmaceutical ingredient and propylene carbonate (≥99.7%, Carl Roth GmbH+Co. KG, Karlsruhe, Germany) in the amounts as given in the following table were mixed in a 5 mL glass vial and solved by using an ultrasonic bath for 20 min at a temperature of 25° C. The mesoporous silica Silsol® (Grace GmbH, Worms, Germany) was added and mixed with a metal spatula until the solution was adsorbed by the silica. The liquisolid pharmaceutical formulations were used immediately for biphasic dissolutions tests.

TABLE 2

Compositions of liquisolid formulations

| Compounds | Dissolution 1 Amounts | Dissolution 2 Amounts | Dissolution 3 Amounts |
|---|---|---|---|
| Nimodipine | 10.9 mg | 10.0 mg | 11.0 mg |
| Propylene Carbonate | 125 μL | 125 μL | 125 μL |
| Silsol ® | 187.3 mg | 188.2 mg | 189.4 mg |
| Celecoxib | 10.9 mg | 10.3 mg | 10.9 mg |
| Propylene Carbonate | 50 μL | 50 μL | 50 μL |
| Silsol ® | 74.0 mg | 75.1 mg | 75.0 mg |
| Fenofibrate | 10.1 mg | 10.0 mg | 10.5 mg |
| Propylene Carbonate | 75 μL | 75 μL | 75 μL |
| Silsol ® | 113.9 mg | 113.2 mg | 113.8 mg |
| Naproxen | 10.4 mg | 10.1 mg | 10.0 mg |
| Propylene Carbonate | 325 μL | 325 μL | 325 μL |
| Silsol ® | 488.2 mg | 488.5 mg | 489.2 mg |
| Loratadine | 10.0 mg | 10.3 mg | 11.0 mg |
| Propylene Parbonate | 175 μL | 175 μL | 175 μL |
| Silsol ® | 263.2 mg | 263.9 mg | 263.4 mg |

EXAMPLE 3: BIPHASIC DISSOLUTION TESTS

The in vivo performance of the liquisolid formulations of poorly water-soluble drugs as prepared in example 2 were investigated by the biphasic dissolution apparatus (BiPHa+) and setup. This approach was chosen to simulate the gastrointestinal properties to obtain in vivo predictive results.

3.1 Method

Biphasic release is a process in which, in addition to solubility in an aqueous medium, adsorption into the intestinal wall is demonstrated using an organic phase. The transition to the organic phase can be understood as absorption of active substances into the blood. The biphasic release experiments were investigated using a fully automated biphasic dissolution apparatus (BiPHa+) as described in A. Denninger et al., Pharmaceutics 2020, 12, 237.

To simulate the gastrointestinal properties to obtain in vivo predictive results, the pH-profile, bile salt concentration and gastrointestinal passage time were adjusted in the aqueous phase to mimic human gut conditions. An organic phase of 1-decanol above the aqueous phase imitated the fraction absorbed from the gut. As a test model, the profile of a person without prior food intake was chosen. Therefore, FaSSIF-V2 medium, which represents the bile salts concentration of a fasted human was used. FaSSIF-V2 medium is a mixture of a phosphate and a citrate buffer system, which facilitates comparable in vivo buffer capacities. To generate an in-situ biorelevant aqueous medium for the fasted state, biorelevant surfactants, namely sodium-taurocholate (3 mM) and lecithin (0.2 mM), were added.

Prior to the start of the experiments, both phases, 1-decanol and the acidic aqueous phase, were saturated with each other. First, the respective formulation was added (Table 2) to 50 mL HCl (0.1 M), simulating the stomach. During the first 30 min the formulation disintegrated/dispersed in 50 ml of 0.1 M HCl. After 30 min FaSSIF-V2 concentrate (sodium-taurocholate and lecithin) was added simultaneously to the addition of citrate-phosphate buffer (tri-potassium phosphate and potassium citrate) resulting in a first pH-shift from pH 1 to pH 5.5, simulating the duodenum. Thereafter, 50 mL 1-decanol was added. The last pH-shift from 5.5 to 6.8 after 90 minutes was gradually adjusted by adding more citrate-phosphate buffer, representing the jejunum and ileum (final concentrations: 3 mM sodium-taurocholate, 0.2 mM lecithin, 525 mM tri-potassium phosphate and 225 M potassium citrate). The adjusted buffers were titrated by 0.1 M NaOH and 0.1 M HCl (pH 5.5-6.8). The whole dissolution took 4.5 hours.

The concentration profiles of the aqueous and organic phase were measured online continuously with an Agilent 8454 UV-Vis spectrometer (Waldbronn, Germany) and quantified on the compound-specific wavelength.

For each compound, the biphasic dissolution test was performed in triplicate. In order to evaluate the liquisolid formulations in terms of their performance, each liquisolid formulation was compared to a respective commercially available formulation.

3.2 Nimodipine

The liquisolid formulation of nimodipine, as described in example 2, was compared to the commercially available market formulation Nimotop® (Bayer Vital GmbH, Leverkusen, Germany).

The FIG. 2 illustrates the pH profile and the biphasic dissolution profiles of the liquisolid formulation of nimodipine in propylene carbonate on Silsol® (PC-Silsol) and the nimodipine market formulation (Market Formulation) during the 270 min dissolution test. As can be taken from FIG. 2, the nimodipine market formulation Nimotop® provided 38% predicted absorption, while the liquisolid formulation of nimodipine provided 46% predicted absorption. Further, the liquisolid formulation of nimodipine showed a different kinetic profile, providing a faster onset of action.

3.3 Celecoxib

The liquisolid formulation of celecoxib, as described in example 2, was compared to the commercially available market formulation Celebrex® (Pfizer Pharma GmbH, Berlin, Germany).

FIG. 3 illustrates the biphasic dissolution profiles of the liquisolid formulation of celecoxib in propylene carbonate on Silsol® (PC-Silsol) and the celecoxib market formulation (Market Formulation) during the 270 min dissolution test. As can be taken from FIG. 3, the celecoxib market formulation Celebrex® provided 41% predicted absorption, while the liquisolid formulation of celecoxib provided 54% predicted absorption. Further, the liquisolid formulation of celecoxib showed a different kinetic profile, providing a faster onset of action.

3.4 Fenofibrate

The liquisolid formulation of fenofibrate, as described in example 2, was compared to the commercially available market formulation Lipidil® (Mylan Healthcare GmbH, Bad Homburg, Germany).

FIG. 4 illustrates the biphasic dissolution profiles of the liquisolid formulation of fenofibrate in propylene carbonate on Silsol® (PC-Silsol) and the fenofibrate market formulation (Market Formulation) during the 270 min dissolution test. As can be taken from FIG. 3, both, the fenofibrate market formulation Lipidil® and the liquisolid formulation of fenofibrate provided 45% predicted absorption. Further, both formulations of fenofibrate showed a kinetic profile, providing a fast onset of action.

3.5 Naproxen

The liquisolid formulation of naproxen, as described in example 2, was compared to the commercially available market formulation Dolormin GS® (Johnson & Johnson GmbH, Neuss, Germany).

FIG. 5 illustrates the biphasic dissolution profiles of the liquisolid formulation of naproxen in propylene carbonate on Silsol® (PC-Silsol) and the naproxen market formulation (Market Formulation) during the 270 min dissolution test. As can be taken from FIG. 5, the naproxen market formulation Dolormin GS® provided 89% predicted absorption, while the liquisolid formulation of naproxen provided 94% predicted absorption. Further, the liquisolid formulation of naproxen showed a kinetic profile, providing a fast onset of action.

3.6 Loratadine

The liquisolid formulation of loratadine, as described in example 2, was compared to the commercially available market formulation Lorano® akut (Hexal AG, Holzkirchen, Germany).

FIG. 6 illustrates the biphasic dissolution profiles of the liquisolid formulation of loratadine in propylene carbonate on Silsol® (PC-Silsol) and the loratadine market formulation (Market Formulation) during the 270 min dissolution test. As can be taken from FIG. 6, the loratadine market formulation Lorano® provided 34% predicted absorption, while the liquisolid formulation of loratadine provided 42% predicted absorption. Further, the liquisolid formulation of loratadine showed a steeper curve in the second half of the biphasic dissolution.

As can be seen from FIGS. 2 to 6, the liquisolid pharmaceutical formulations of poorly water-soluble drugs in propylene carbonate adsorbed onto mesoporous silica provided improved absorption of the active ingredient compared to the available market formulations.

Example for Comparison 4: Testing of Liquisolid Formulation Manufactured Using Various Non-Volatile Solvents 4.1 Solubility Screening The solubility of the poorly water-soluble APIs celecoxib, fenofibrate, naproxen, loratadine, and nimodipine in tetraglycole (TEG), polyethylene glycol 400 (PEG 400) propylene glycol (PG) and glycerol was evaluated as described in Example 1. Therefore, 1 mg of each compound was weighted in an Eppendorf tube and 1 ml of solvent was added. The mixture was mixed with a metal spatula for 10 min each. The solubility of compounds, which were fully dissolved in the preliminary tests where than further analyzed. About 20 mg of each compound were used and under stirring with a metal spatula the solvent was added in 10 µl steps. The used APIs are listed in table 3. The used solvents are summarised in Table 4.

TABLE 3

| Active pharmaceutical ingredients (API) | |
|---|---|
| API | Supplier |
| Celecoxib | Kekule Pharma Limited, Hyderabad, India |
| Fenofibrate | Sigma-Aldrich Chemie GmbH, Steinheim, Germany |
| Naproxen | Sigma-Aldrich Chemie GmbH, Steinheim, Germany |
| Loratadine | Sris Pharmaceuticals, Hyderabad, India |
| Nimodipine | Tokyo Chemical Industrie, Zwijndrecht, Belgium |

TABLE 4

| Non-volatile solvents | |
|---|---|
| non-volatile solvent | Supplier |
| tetraglycole (TEG) | Sigma-Aldrich Chemie GmbH (Taufkirchen, Germany) |
| polyethylene glycol 400 (PEG 400) | Carl Roth GmbH + Co. KG |
| propylene glycol (PG) | Carl Roth GmbH + Co. KG |
| glycerol | Caesar & Loretz GmbH (Hilden, Germany) |

The following table 5 shows the results of the solubility tests.

TABLE 5

Solubility of poorly water-soluble active pharmaceutical ingredients (API) in non-volatile solvents.

| | Solubility (mg/mL) | | | |
|---|---|---|---|---|
| API | TEG | PEG 400 | PG | Glycerol |
| Celecoxib | 244.31 | 230.12 | 60.29 | <1 |
| Fenofibrate | 212.34 | 150.14 | 12.13 | <1 |
| Naproxen | 285.21 | 102.34 | 31.24 | <1 |
| Loratadine | 105.29 | 60.98 | 59.14 | <1 |
| Nimodipine | 140.13 | 96.31 | 25.45 | <1 |

As can be taken from Table 5, also tetraglycole (TEG) has been found to dissolve the APIs sufficiently to prepare liquisolid formulations. Furthermore, polyethylene glycol 400 (PEG 400) dissolved the APIs sufficiently. Propylene glycol (PG) dissolved only loratadine sufficiently to prepare a comparable liquisolid formulation. Glycerol was found to be not suitable due a solubility of less than 1 mg/mL.

4.2: Manufacture of Liquisolid Pharmaceutical Formulations by Adsorption to Mesoporous Silica Using Various Non-Volatile Solvents Mesoporous silica based formulations with poorly aqueous soluble APIs as summarised in Table 3 and the non-volatile solvents tetraethylene glycol (TEG), polyethylene glycol 400 (PEG 400) and propylene glycol (PG) were prepared as described in Example 2.

The active pharmaceutical ingredient and the respective amount of non-volatile solvent in the amounts as given in the following Tables 6, 7, 8, 9 and 10 were mixed in a 10 mL screw lid glass vial and solved by using an ultrasonic bath for 20 min at a temperature of 25° C. The mesoporous silica Silsol® (Lot. 1000306729; W. R. Grace & Co.-Conn. Europe, Worms, Germany) was added and mixed with a metal spatula until the solution was adsorbed by the silica. The liquisolid pharmaceutical formulations were used immediately for biphasic dissolutions tests.

Table 6: Composition of liquisolid celecoxib formulations.

TABLE 6

Composition of liquisolid celecoxib formulations.

| Compounds | Dissolution 1 Amounts | Dissolution 2 Amounts | Dissolution 3 Amounts |
|---|---|---|---|
| Celecoxib | 10.6 mg | 10.0 mg | 10.1 mg |
| TEG | 50 µL | 50 µL | 50 µL |
| Silsol ® | 75.2 mg | 75.1 mg | 76.1 mg |
| Celecoxib | 10.1 mg | 10.4 mg | 10.1 mg |
| PEG 400 | 50 µL | 50 µL | 50 µL |
| Silsol ® | 74.3 mg | 76.1 mg | 75.9 mg |

TABLE 7

Composition of liquisolid fenofibrate formulations.

| Compounds | Dissolution 1 Amounts | Dissolution 2 Amounts | Dissolution 3 Amounts |
|---|---|---|---|
| Fenofibrate | 10.6 mg | 9.4 mg | 9.9 mg |
| TEG | 75 µL | 75 µL | 75 µL |
| Silsol ® | 111.4 mg | 115.0 mg | 113.8 mg |
| Fenofibrate | 10.3 mg | 10.3 mg | 10.6 mg |
| PEG 400 | 75 µL | 75 µL | 75 µL |
| Silsol ® | 114.3 mg | 114.0 mg | 113.9 mg |

TABLE 8

Composition of liquisolid naproxen formulations.

| Compounds | Dissolution 1 Amounts | Dissolution 2 Amounts | Dissolution 3 Amounts |
|---|---|---|---|
| Naproxen | 10.5 mg | 10.6 mg | 11.0 mg |
| TEG | 325 µL | 325 µL | 325 µL |
| Silsol ® | 486.6 mg | 484.0 mg | 486.8 mg |
| Naproxen | 10.2 mg | 10.2 mg | 10.6 mg |
| PEG 400 | 325 µL | 325 µL | 325 µL |
| Silsol ® | 489.3 mg | 487.9 mg | 487.1 mg |

TABLE 9

Composition of liquisolid loratadine formulations.

| Compounds | Dissolution 1 Amounts | Dissolution 2 Amounts | Dissolution 3 Amounts |
|---|---|---|---|
| Loratadine | 9.8 mg | 10.7 mg | 10.6 mg |
| TEG | 175 µL | 175 µL | 175 µL |
| Silsol ® | 264.4 mg | 260.2 mg | 263.9 mg |
| Loratadine | 9.6 mg | 10.0 mg | 10.0 mg |
| PEG 400 | 175 µL | 175 µL | 175 µL |
| Silsol ® | 266.8 mg | 261.2 mg | 263.9 mg |
| Loratadine | 9.9 mg | 10.0 mg | 10.0 mg |
| PG | 175 µL | 175 µL | 175 µL |
| Silsol ® | 286.2 mg | 261.4 mg | 265.2 mg |

TABLE 10

Composition of liquisolid nimodipine formulations.

| Compounds | Dissolution 1 Amounts | Dissolution 2 Amounts | Dissolution 3 Amounts |
|---|---|---|---|
| Nimodipine | 10.4 mg | 10.2 mg | 10.3 mg |
| TEG | 125 μL | 125 μL | 125 μL |
| Silsol ® | 187.0 mg | 190.5 mg | 191.2 mg |
| Nimodipine | 10.9 mg | 9.4 mg | 9.3 mg |
| PEG 400 | 125 μL | 125 μL | 125 μL |
| Silsol ® | 186.6 mg | 190.5 mg | 186.3 mg |

4.3: Biphasic Dissolution Tests of Liquisolid Formulation Manufactured Using Various Non-Volatile Solvents To evaluate the performance of the prepared formulations in vitro biphasic dissolution tests were performed via the BiPHa+ as described in Example 3. The maximum partitioned drug in the organic phase in vitro has the ability to estimate the fraction absorbed in vivo, due to the selected biorelevant method setup simulating human GIT conditions. The market formulations (Originator) of the selected APIs were tested additionally to compare the performance against established marked products. The market formulations (Originator) as summarised in the following table 11 were used:

TABLE 11

Used market formulations of the active pharmaceutical ingredients (APIs)

| API | Market Formulation | Supplier |
|---|---|---|
| Celecoxib | Celebrex ® | Pfizer Pharma GmbH (Berlin, Germany) |
| Fenofibrate | Lipidil ® | Mylan Healthcare GmbH (Bad Homburg, Germany |
| Naproxen | Dolormin GS ® | Johnson & Johnson GmbH (Neuss, Germany) |
| Loratadine | Lorano ® akut | Hexal AG (Holzkirchen, Germany) |
| Nimodipine | Nimotop ® | Bayer Vital GmbH (Leverkusen, Germany) |

The results of the biphasic dissolutions represented by the maximum partitioned drug (%) in the organic phase are summarised in the following table 12 and compared to the results for propylene carbonate (PC) as determined in examples 3.2 to 3.6.

TABLE 12

Biphasic dissolution results: maximum partitioned drug in the organic phase.

| | Maximum Partitioned Drug in the Organic Phase (%) | | | | |
|---|---|---|---|---|---|
| API | PC Silsol ® Formulation | TEG Silsol ® Formulation | PEG 400 Silsol ® Formulation | PG Silsol ® Formulation | Market Formulation |
| Celecoxib | 54 | 53 | 46 | * | 41 |
| Fenofibrate | 45 | 28 | 32 | * | 45 |
| Naproxen | 94 | 86 | 69 | * | 89 |
| Loratadine | 42 | 38 | 23 | 38 | 34 |
| Nimodipine | 46 | 38 | 32 | * | 38 |

*Poor solubility of the API in the solvent, therefore, not feasible for formulation.

As can be taken from the table 12, the formulations where the API was dissolved in propylene carbonate demonstrated the best performance regarding the dissolution and solubility properties for all tested APIs.

The corresponding marked formulations were also analyzed under the same in vitro conditions and revealed that the formulations using propylene carbonate were comparable for fenofibrate, and for the further APIs celecoxib, naproxen, loratadine, and nimodipine showed even better results than the commercially available formulations.

The invention claimed is:

1. A liquisolid pharmaceutical formulation comprising a porous carrier and an active pharmaceutical ingredient loaded onto a surface of the porous carrier, wherein the active pharmaceutical ingredient is dispersed in propylene carbonate or a mixture of propylene carbonate and a further solvent and the dispersion of the active pharmaceutical ingredient and propylene carbonate or a mixture of propylene carbonate and a further solvent is loaded onto the external surface and the internal surface located inside the pores of the porous carrier thereby forming a liquisolid system, wherein the active pharmaceutical ingredient is loaded to the porous carrier in an amount in a range of ≥5 weight % to ≤70 weight %, based on a weight of 100 weight % of the liquisolid pharmaceutical formulation comprising the porous carrier, the active pharmaceutical ingredient and propylene carbonate.

2. The liquisolid pharmaceutical formulation according to claim 1, wherein the porous carrier is selected from the group consisting of porous silica, polyorganosiloxanes, pharmaceutical clays, silicon dioxide nanotubes, silica gel, magnesium aluminosilicate, anhydrous calcium phosphate, and calcium carbonate.

3. The liquisolid pharmaceutical formulation according to claim 2, wherein the porous carrier is mesoporous silica.

4. The liquisolid pharmaceutical formulation according to claim 1, wherein the further solvent is selected from the group consisting of dimethyl sulfoxide, ethanol, methanol, isopropanol, dichloromethane, acetone, tert-butanol, and a polymer which is liquid at ambient temperature.

5. The liquisolid pharmaceutical formulation according to claim 1, wherein the active pharmaceutical ingredient is a poorly water-soluble or water-insoluble compound.

6. A liquisolid pharmaceutical formulation comprising a porous carrier and an active pharmaceutical ingredient loaded onto a surface of the porous carrier, wherein the active pharmaceutical ingredient is dispersed in propylene carbonate or a mixture of propylene carbonate and a further solvent and the dispersion of the active pharmaceutical ingredient and propylene carbonate or a mixture of propylene carbonate and a further solvent is loaded onto the external surface and the internal surface located inside the pores of the porous carrier thereby forming a liquisolid system, wherein propylene carbonate is in an amount in a range of ≥10 weight % to ≤60 weight %, based on a weight of 100 weight % of the porous carrier and propylene carbonate.

7. A pharmaceutical solid dosage form according to claim 1, comprising the liquisolid pharmaceutical formulation according to claim 1.

8. The pharmaceutical solid dosage form according to claim 7, wherein the compound is selected from the group consisting of a capsule, a tablet, granules, pills, pellets and micro-tablets.

9. A process for manufacturing a liquisolid pharmaceutical formulation, the process comprising the steps of:

a) dispersing, dissolving or otherwise introducing an active pharmaceutical ingredient into propylene carbonate or a mixture of propylene carbonate and a further solvent to form a liquid mixture, b) selecting a porous carrier, and c) admixing the liquid mixture of step a) and the porous carrier of step b) to form a liquisolid formulation, wherein the active pharmaceutical ingredient is loaded to the porous carrier in an amount in a range of ≥5 weight % to ≤70 weight %, based on a weight of 100 weight % of the liquisolid pharmaceutical formulation comprising the porous carrier, the active pharmaceutical ingredient and propylene carbonate.

10. The process according to claim 9, wherein in a further step d) the liquisolid formulation is formed into capsules, tablets, granules, pills, pellets or micro-tablets.

11. The process according to claim 9, wherein the admixing in step c) is performed at a temperature in a range from ≥10° C. to ≤50° C.

12. The process according to claim 9, wherein in step a) the dispersing, dissolving or otherwise introducing an active pharmaceutical ingredient into propylene carbonate or a mixture of propylene carbonate and a further solvent is performed by ultrasonic dissolving, vortexing, or mixing using magnetic mixers or blade agitators.

13. A liquisolid pharmaceutical formulation or a pharmaceutical solid dosage form obtained by the process according to claim 9.

14. The liquisolid pharmaceutical formulation of claim 4, wherein the further solvent is polyethylene glycol.

15. The liquisolid pharmaceutical formulation of claim 5, wherein the active pharmaceutical ingredient is selected from the group consisting of nimodipine, celecoxib, fenofibrate, naproxen, loratadine, imipramine, bisacodyl, gliclazide, furosemide, clozapine and mixtures thereof.

16. The liquisolid pharmaceutical formulation of claim 1, wherein the active pharmaceutical ingredient is loaded to the porous carrier in an amount in a range of ≥20 weight % to ≤50 weight %, based on a weight of 100 weight % of the liquisolid pharmaceutical formulation comprising the porous carrier, the active pharmaceutical ingredient and propylene carbonate.

17. The liquisolid pharmaceutical formulation of claim 6, wherein propylene carbonate is comprised in an amount in a range of ≥30 weight % to ≤50 weight %, based on a weight of 100 weight % of the porous carrier and propylene carbonate.

18. The method of claim 11, wherein the admixing in step c) is performed at a temperature in a range from ≥15° C. to ≤30° C.

19. The liquisolid pharmaceutical formulation according to claim 6, wherein the porous carrier is selected from the group consisting of porous silica, polyorganosiloxanes, pharmaceutical clays, silicon dioxide nanotubes, silica gel, magnesium aluminosilicate, anhydrous calcium phosphate, and calcium carbonate.

20. The liquisolid pharmaceutical formulation according to claim 19, wherein the porous carrier is mesoporous silica.

* * * * *